US009314511B2

(12) United States Patent
Keimel (10) Patent No.: US 9,314,511 B2
(45) Date of Patent: Apr. 19, 2016

(54) METHOD FOR TREATMENT OF CARDIAC DISORDERS (71) Applicant: MEDTRONIC, INC., Minneapolis, MN (US)

(72) Inventor: John G. Keimel, North Oaks, MN (US)

(73) Assignee: Medtronic, Inc., Minneapolis, MN (US)

( * ) Notice: Subject to any disclaimer, the term of this patent is extended or adjusted under 35 U.S.C. 154(b) by 164 days.

(21) Appl. No.: 13/940,453

(22) Filed: Jul. 12, 2013

(65) Prior Publication Data
US 2014/0012230 A1   Jan. 9, 2014

Related U.S. Application Data

(63) Continuation of application No. 11/124,984, filed on May 9, 2005, now Pat. No. 8,500,720.

(51) Int. Cl.
| | |
|---|---|
| *A61K 38/47* | (2006.01) |
| *A61M 5/142* | (2006.01) |
| *A61K 31/713* | (2006.01) |
| *A61M 5/172* | (2006.01) |
| *A61M 39/02* | (2006.01) |
| *A61M 39/04* | (2006.01) |
| *A61K 38/00* | (2006.01) |

(52) U.S. Cl.
CPC ............. *A61K 38/47* (2013.01); *A61K 31/713* (2013.01); *A61M 5/14276* (2013.01); *A61K 38/00* (2013.01); *A61M 5/172* (2013.01); *A61M 39/0208* (2013.01); *A61M 39/04* (2013.01); *A61M 2210/125* (2013.01)

(58) Field of Classification Search
CPC ............ A61M 5/14276; A61M 5/172; A61M 2210/125; A61K 31/713; A61K 38/00; A61K 38/47
See application file for complete search history.

(56) References Cited

U.S. PATENT DOCUMENTS

| | | | | |
|---|---|---|---|---|
| 3,923,060 | A | * | 12/1975 | Ellinwood, Jr. ............ 604/891.1 |
| 4,146,029 | A | | 3/1979 | Ellinwood |
| 5,057,301 | A | | 10/1991 | Wilbur |
| 5,222,982 | A | | 6/1993 | Ommaya |
| 5,269,326 | A | | 12/1993 | Verrier |
| 5,385,582 | A | | 1/1995 | Ommaya |
| 5,433,946 | A | | 7/1995 | Allen, Jr. |
| 5,690,682 | A | | 11/1997 | Buscemi |

(Continued)

FOREIGN PATENT DOCUMENTS

| | | |
|---|---|---|
| FR | 2637807 | 4/1990 |
| WO | WO 01/34088 | 5/2001 |

OTHER PUBLICATIONS

Chian, R. et al., "Insulin-Like Growth Factor-1: Tetanus Fragment C Fusion Protein for Improved Delivery of IGF-1 to the CNS," Washington, DC: Society for Neuroscience, Program No. 413.14, Abstract Viewer/Itinerary Planner (2003).
Dobrenis K. et al., "Neuronal Lysosomal Enzyme Replacement Using Fragment C of Tetanus Toxin", Proc. Natl Acad Sci USA, vol. 89, No. 5, p. 2297-301 (Mar. 15, 1992).

(Continued)

*Primary Examiner* — Andrew Gilbert
(74) *Attorney, Agent, or Firm* — Carol F. Barry (57) ABSTRACT

The present invention is directed to systems and methods for delivering therapy for a cardiac disorder, wherein the system comprises a source for supplying a protein formulation containing a protein that is otherwise deficient in cardiac cells in a patient with a cardiac disorder, and a catheter having a proximal end and a distal end for delivering the protein formulation to the pericardial sac region of a human heart.

9 Claims, 4 Drawing Sheets

(56) References Cited

U.S. PATENT DOCUMENTS

| | | | |
|---|---|---|---|
| 5,792,110 | A | 8/1998 | Cunningham |
| 5,798,366 | A | 8/1998 | Platt |
| 5,814,014 | A | 9/1998 | Elsberry |
| 5,817,131 | A | 10/1998 | Elsberry |
| 5,925,066 | A | 7/1999 | Kroll |
| 6,093,180 | A | 7/2000 | Elsberry |
| 6,200,303 | B1 | 3/2001 | Verrior |
| 6,206,004 | B1 | 3/2001 | Schmidt |
| 6,410,250 | B1 | 6/2002 | Gueiros-Filho |
| 6,569,661 | B1 | 5/2003 | Qin et al. |
| 6,582,692 | B1 | 6/2003 | Podsakoff |
| 6,585,971 | B1 | 7/2003 | Kakkis |
| 6,592,519 | B1 * | 7/2003 | Martinez ................ 600/309 |
| 6,635,049 | B1 | 10/2003 | Robinson |
| 6,638,712 | B2 | 10/2003 | Lobel et al. |
| 6,666,844 | B1 | 12/2003 | Igo |
| 6,858,206 | B2 | 2/2005 | Kakkis |
| 7,022,321 | B2 * | 4/2006 | Eglitis ............... C07K 14/475 424/93.1 |
| 8,500,720 | B2 * | 8/2013 | Keimel ................ 604/891.1 |
| 2003/0009145 | A1 * | 1/2003 | Struijker-Boudier et al. 604/500 |
| 2003/0129186 | A1 | 7/2003 | Beliveau |
| 2003/0228284 | A1 * | 12/2003 | McCown ............ A61K 48/005 424/93.2 |
| 2005/0208090 | A1 * | 9/2005 | Keimel ............ A61K 38/1709 424/423 |
| 2005/0281805 | A1 * | 12/2005 | LeBowitz et al. ......... 424/94.61 |
| 2006/0240440 | A1 * | 10/2006 | Stafford et al. ................ 435/6 |
| 2006/0251641 | A1 * | 11/2006 | Keimel ................ 424/94.61 |
| 2011/0213328 | A1 * | 9/2011 | Keimel et al. ................ 604/500 |
| 2014/0012230 | A1 * | 1/2014 | Keimel ................ 604/506 |

OTHER PUBLICATIONS

Hsu et al. "Aniemann-Pick Disease Type C Treated by Bone Marrow Transplantation", Bone Marrow Transplantation, vol. 24, pp. 103-107 (1999).

Kakkis, E., Normalization of Carbohydrate Storage in Brain Tissue Using an MPS 1 Model, Ninth International Congress on Inborn Errors of Metabolism, Sep. 3, 2003, Brisbane Australia (BioMarin Pharmaceutical Inc. Press Release dated Sep. 4, 2003).

Kmiec, "Gene Therapy," American Scientist, vol. 87, No. 3, p. 240 (1999).

Larson, K.E., et al. "Glial-Derived Neurotrophic Factor: Tetanus Toxin Fragment C Fusion Protein for Targeted Delivery of GDNF to Neurons", Washington, DC: Society for Neuroscience, Program No. 733.18, Abstract Viewer/Intinerary Planner (2003).

Matthews, C.C. et al., "A Streptavidin-Tetanus Toxin C Fragment Fusion Protein for the Delivery of Biotinylated Molecules to Neuronis," Washington, DD Society for Neuroscience, Program No. 733.18, Abstract Viewer/Itinerary Planner (2003).

Von Specht, B.U. et al., "Enzyme Replacement in Tay-Sachs Disease", Neurology, vol. 29, No. 6, p. 848-54 (Jun. 1979).

Willerson, J.T. et al., "The Genetic Basis of Cardiovascular Disease", Cardiovascular Medicine, Churchill Livingstone, NY, p. 1660-2 (1995).

Yaeger et al., "Bone Marrow Transplantation for Infantile Ceramidase Deficiency (Farber Disease)," Bone Marrow Transplantation, vol. 29, p. 357-363 (2000).

Zipes, et al., "Molecular Genetics and Pharmacogenomics", Cardiac Electrophysiology: From cell to Bedside, Saunders, Philadelphia, PA, Part X, p. 452-463 (2004).

Zirzow, G.C., et al. "Delivery, Distribution and Neuronal Uptake of Exogenous Mannose-Terminal Gluccocerebrosidase in the Intact Rat Brain", Neurochem Res., vol. 24, No. 2, p. 301-5 (Feb. 1999).

* cited by examiner

METHOD FOR TREATMENT OF CARDIAC DISORDERS

This application is a continuation of U.S. application Ser. No. 11/124,984, filed May 9, 2005, now U.S. Pat. No. 8,500,720, the disclosure of which is incorporated by reference herein in its entirety.

BACKGROUND OF THE INVENTION

The present invention pertains to medical devices and methods for the treatment of cardiac disorders by delivering a therapeutic protein formulation to the pericardial sac region of the heart.

Deoxyribonucleic acid, or DNA, contains the hereditary information passed onto all offspring. The sequential information contained in DNA is used to guide the synthesis of other molecules called proteins, which are long unbranched polymer chains of amino acids. A gene is defined as the segment of DNA sequence corresponding to a single protein. Proteins are the primary functional unit of human cells and have a host of functions including catalyzing reactions (enzymes), maintaining structure, generating movement, and sensing signals. Each protein performs a specific function according to its genetically specified sequence of amino acids. Genetic mutations can lead to mutations in the amino acid sequence of the associated protein that, in turn, can lead to inadequate or abnormal function of the protein. These modifications of proteins can cause major illness and disease.

A gene mutation can be inherited from parents or caused by a number of factors including environmental agents such as radiation, chemicals, and viruses. As a consequence of the gene mutation, the corresponding mutated protein is absent or deficient in its level of activity, loses its ability to regulate cellular processes, or has a nonfunctional structure. These protein deficiencies are known to be the cause of many diseases, including many cardiac diseases. One category of cardiac diseases is inborn errors of metabolism, which includes amino acidopathies, urea cycle defects, lysosomal storage disorders, and fatty acid oxidation defects. Using lysosomal storage diseases as an example, the protein (enzyme) deficiency results in the toxic accumulation of substrates at the point of the blocked metabolic path, accumulation of toxic intermediates from an alternative pathway, or toxicity caused by a deficiency of products beyond the blocked point. The degree of metabolic deficiency, which is related to the degree of protein deficiency, is a major factor in the clinical manifestation (phenotype) and severity of the disease. Many of these protein deficiency diseases have an effect on cardiac cells (See Table 1).

One focus for treating protein deficiency diseases has been to administer the missing enzyme to the patient suffering from the corresponding enzyme deficiency. Such enzyme replacement therapy (ERT) can be accomplished by administering an isolated or synthetic form of the enzyme (e.g. a recombinant protein) to the patient. Intravenous or other systemic administration of an enzyme as ERT can be effective in treating some disease symptoms. ERT has been especially effective in diseases, such as Gaucher Disease, which primarily affects the liver and spleen, because the proteins are quickly taken-up from the bloodstream by these organs.

Other lysosomal storage diseases are not treated adequately with ERT because of the limited take-up of the proteins by the effected organ or tissue. ERT is not as effective in treating cardiac aspects of Pompe Disease, a lysosomal storage disease, because of the large mass of the heart and the difficulty of this large mass of tissue taking-up the replacement enzymes in the short time these enzymes are available in the bloodstream. This traditional type of ERT can therefore be costly and ineffective due to the mass amounts of enzyme needed, the possibility of poor results due to the enzyme uptake by other organs, and failure of the cardiac cells to import the enzyme once received.

One way of addressing the problems of delivery of the deficient enzyme to the heart cells of patients suffering from these diseases is by gene therapy. Gene therapy for cardiac disorders involves genetically engineering the DNA coding sequence for the deficient enzyme into a non-viral or viral vector, then surgically injecting the vector into the heart, after which the cells transfected by the vector produce the missing enzyme and may secrete it to adjacent tissues. See Kmiec, Gene Therapy, American Scientist, 87 (3): 240 (1999). To date, although this approach has been demonstrated to be feasible in animal models, it has not yet been proven effective in treating cardiac disorders in humans.

There have also been attempts to treat patients with enzyme deficient diseases by providing the needed enzymes through bone marrow transplants. See Hsu et al., Niemann-Pick disease type C (a cellular cholesterol lipidosis) treated by bone marrow transplantation," Bone Marrow Transplantation, 24:103-107 (1999); Yeager et al., "Bone marrow transplantation for infantile ceramidase deficiency (Farber disease)," Bone Marrow Transplantation, 26:357-363 (2000). Such attempts are based on the premise that undifferentiated stem cells originating from implanted bone marrow will develop into and replace the genetically defective cardiac cells that cause a particular cardiac disorder. While this type of therapy may be effective in some diseases, the high morbidity associated with this procedure has prevented its widespread use in all but a few of the most serious diseases.

Another way of addressing delivery of the deficient enzyme to the heart is by direct "manual" injection or injection into the blood stream so the therapeutic compound can find its way into the heart. Based upon the results, this type of remedy still does not overcome the inefficiencies of cellular uptake of the enzyme. Even if effective, systemic delivery would require the repeated administration of large amounts of expensive enzymes with only a small percentage of these enzymes ultimately reaching the area of the heart that is targeted.

Additionally, a potential problem in the treatment of cardiac diseases is the possibility of toxic build-up and serious side effects of downstream metabolic byproducts upon initial treatment with the missing enzyme. This occurs when the sudden availability of the missing enzyme, and the presence of the accumulated substrate for it, results in the rapid production of downstream metabolic byproducts of the previously blocked step, overwhelming the ability of the enzymes in the downstream pathways to perform their downstream steps. As a consequence, other metabolic intermediates can temporarily accumulate to levels sufficient to cause cardiac damage.

Thus, methods, devices, and systems for delivering enhanced proteins and enzymes to the heart at precise levels for long-term therapies remain an elusive challenge.

BRIEF SUMMARY OF THE INVENTION

The present invention is directed to methods, devices, and systems for the treatment of deficient or abnormal enzymes or proteins within the cells of the heart. The invention has application in the cardiac aspects of the broad category of protein deficiency or abnormality diseases. These diseases are the result of insufficient enzyme/protein activity or the lack of a specific enzyme/protein in cardiac cells.

The present invention uses an implantable source and catheter to deliver a therapeutic protein formulation containing a protein in a form that is deficient in cardiac cells in a patient with a cardiac disorder. The protein formulation is delivered by the catheter to a pericardial sac region of the heart.

DETAILED DESCRIPTION

Figure 1:
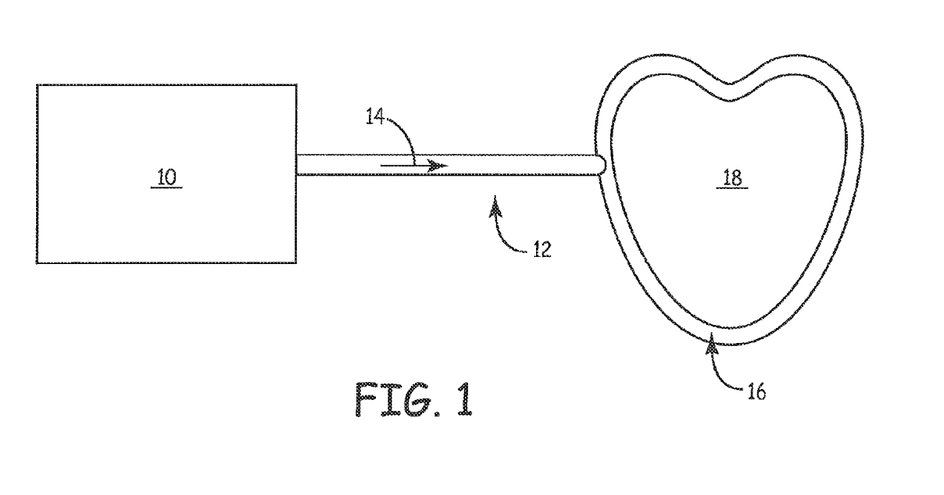
FIG. 1 is a schematic representation of the present invention, including an implantable source that delivers a therapeutic protein formulation to the pericardial sac region through a catheter.

FIG. 1 is a schematic illustration of the present invention, in which implantable source 10 and catheter 12 deliver therapeutic protein formulation 14 (represented as an arrow) to pericardial sac 16 surrounding heart 18. Implantable source 10 is a pump that delivers formulation 14 under pressure to catheter 12, or is an access port into which formulation 14 is injected using a syringe and thereby delivers formulation 14 by the pressure exerted through the plunger of the syringe. Catheter 12 has its proximal end connected to source 10 and its distal end inserted into pericardial sac 16.

Pericardial sac 16 prevents dilatation of the chambers of the heart, lubricates the surfaces of the heart, and maintains the heart in a fixed geometric position. It also provides a barrier to the spread of infection from adjacent structures in the chest, and prevents the adhesion of surrounding tissues to heart 18.

Pericardial sac 16 is an ideal delivery point for therapeutic proteins needed to treat a cardiac protein disorder due to the fact that the complete contents of pericardial sac 16 turn over only 2 to 3 times per day. This is much slower than the time required for blood to pass through the heart. Proteins that are delivered intravenously pass through the heart quickly and then are subsequently filtered out of the blood by the liver or absorbed by other tissue. Proteins that are administered intravenously thereby have a relatively short time period when the protein can be in contact with the cardiac cells, and this is thereby an inefficient route for delivering proteins to cardiac cells. The relatively slow turn over of the contents of pericardial sac 16 then allows a greater time for the protein to enter the intercellular space of the heart 18 and enter the cells.

Formulation 14 includes one or more proteins that are deficient in patients being treated for cardiac diseases/disorders. The cardiac diseases are selected from the group consisting of protein deficiency diseases, enzyme deficiency diseases, inborn errors of metabolism, cardiodegenerative diseases, pericardial diseases, hereditary cardiomyopathy diseases, hereditary channelopathy diseases, cardiac protein deficiencies which results from RNA interference therapy, cardiac protein deficiencies caused by environmental factors (radiation, chemicals, and viruses), and combinations thereof.

Formulation 14 comprises proteins that have been formulated for enhanced cellular uptake. Such modified (i.e., enhanced) proteins generally comprise the therapeutic protein or proteins in which the patient is deficient or lacking (or for some reason inactive), and also a transport aid and linker species to which the therapeutic protein is bonded and which facilitates cellular uptake (e.g., endocytosis) of the modified protein into cardiac cells.

The transport aid can be any species that, when conjugated (i.e., associated) with a therapeutic protein of the present invention to form a therapeutic protein formulation, enhances the ability of the therapeutic protein formulation (relative to the protein alone) to penetrate cardiac cell membranes. In one embodiment, the transport aid comprises at least a portion of a species selected from the group consisting of recombinant human melanotransferrin (p97), tetanus toxin fragment C (TTC), endogenous lectins, and combinations thereof.

The bonding of the therapeutic protein with the transport aid may or may not include a covalent bond, and the linker can be selected from the group consisting of peptide linkages, disulfide linkages, and combinations thereof. In one embodiment, a linker species is a streptavidin-biotin complex. The streptavidin-biotin linker complex may be better suited for some therapies as dissociation of the complex, once inside the target cells, can likely be promoted by pH modulation.

For some therapies, stabilizing agents or other anti-degradation agents may be added to the protein formulation in order to prevent dissociation of the proteins by maintaining a physiologically acceptable pH. This is particularly important when the proteins will be stored for a long period of time within the pump.

Identifying and selecting the appropriate protein material to provide for a therapeutic protein formulation, appropriate for use in protein replacement therapy for a particular cardiac disorder, generally entails a suitable diagnosis accompanied by, possibly, one or more diagnostic tests. With inborn errors of metabolism or other genetic diseases, the positive diagnosis can be obtained by molecular analysis with the identification of a genetic mutation.

Table 1, located below, represents a list of metabolic disorders with associated cardiac manifestations and their known or unknown associated protein defect. In one embodiment the listed protein/enzyme, located in the second column of Table 1, represents at least a portion of the protein that will be delivered as formulation 14. In other embodiments, formulation 14 may contain at least a portion of a protein or proteins that are found in cardiac cells.

TABLE 1

| Metabolic Disorders With Cardiovascular Manifestations | | | |
|---|---|---|---|
| Name of Disorder | Defective Protein/Enzyme | Pathology | Cardiovascular Manifestation |
| Mucopolysaccharidoese Hurler (MPS IH) | α-L-iduronidase | Defective degradation of dermatan sulfate and heparin sulfate by lysosomes | HTN, valvular dysfunction, arterial disease |

TABLE 1-continued

Metabolic Disorders With Cardiovascular Manifestations

| Name of Disorder | Defective Protein/Enzyme | Pathology | Cardiovascular Manifestation |
|---|---|---|---|
| Schie (MPS IS) | α-L-iduronidase | Defective degradation of dermatan sulfate and heparin sulfate by lysosomes | AI (Aortic Insufficiency) |
| Hunter (MPS II) | Sulfoiduranate sulfate | Defective degradation of dermatan sulfate and heparin sulfate | HTN, valvular dysfunction, arterial disease |
| Marquio syndrome (Mucopolysaccharidosis II) | β-Galactosidase | Defective degradation of keratan sulfate by lysosomes | Cardiac valvular lesions |
| Maroteaux-Lamy syndrome (MPS VI) | Aryl sulfatase B | Defective degradation of dermatan sulfate by lysosomes | Calcified, stenotic aortic valve |
| Mucolipidoses I-cell disease (Mucolipidosis II) | N-acetyl-glucosamine-I-phosphotransferase | Lysomal enzymes transport in cells is abnormal Leads to impaired lysosomal function | Cardiomegaly, valvular lesions |
| PseudoHurler polydystrophy (Mucolipidoses III) | N-acetyl-glucosamine-I-phophotransferase | Impaired lysosomal function | Valvular lesions |
| Sphingo lipidoses Gaucher disease Type I | Glucocerebrosidase | Accumulation of glycosylceramide in lysosomes leads to tissue injury | Pericardial disease |
| Fabry disease | α-Galactosidase | Intracellular deposition of glycosphingolipids in lysosomes LV | Valvular dysfunction including MVP, MI, hypertrophy, ECG, chages, cerebrovascular involvement, angiokeratoma |
| Glycogen Storage Diseases Type II Glycogenosis (Pompe disease) | Lysosomal acid α-glucosidase | Intracellular accumulation of glycogen | Cardiomegaly, CHF |
| Type III Glycogenosis | Amlo-1.6-glucosidase | Intracellular accumulation of glycogen with shorter outer chains | CHF, sudden death |
| Acyl-CoA Dehydrogenase Deficiencies LCAD Deficiency | Long-chain acylCoA dehydrogenase | Impaired oxidation of long-chain fatty acids | Hypertrophic cardiomyopathy, sudden death |
| Primary Hyperoxaluria Primary hyperoxaluria I | Alumine: glyoxylate amino transferase | Deposition of calcium oxalate crystals (oxalosis) | Complete atrioventricular block |
| Primary hyperoxaluria II | D-glyceric acid dehydrogenase | Deposition of calcium oxalate crystals (oxalosis) | Complete atrioventricular block |
| Abnormalities of Storage of Sterols Other Than Cholesterol Cerebrotendinous xanthomatosis | Hepatic mitochondrial 26-hydroxylase | Block in bile acid synthesis leads to accumulation of cholestanol and cholesterol in tissues | Premature atherosclerosis |
| Phytosterolemia | Unknown autosomal recessive mutation | Increased amounts of phytosterols (plant sterols) in plasma and tissues | Premature atherosclerosis |
| Disorders of Copper Transport Wilson's disease | WD gene | Failure to incorporate copper into ceruloplasmin and failure to excrete copper into bile leads to toxic accumulation of copper in tissues | Cardiomyopathy |
| Menkes disease | MNK gene (copper transporting ATPase enzyme) | Defective intracellular transport leads to deficiency of copper-containing enzymes | Arterial rupture and thrombosis |

TABLE 1-continued

Metabolic Disorders With Cardiovascular Manifestations

| Name of Disorder | Defective Protein/Enzyme | Pathology | Cardiovascular Manifestation |
|---|---|---|---|
| Homocystinuria | Cystathionine β-synthase | Accumulation of homocysteine and methionine in plasma | Thromboembolism affecting large and small arteries and veins |
| Triose-phosphate isomerase deficiency | Triose-phosphate isomerase | Deficiency of triose-phosphate isomerase in all tissues | Sudden cardiac death secondary to arrhythmia |
| Antithrombin deficiency | Antithrombin | Lack of inhibition of activated coagulation of the intrinsic system | Deep venous thrombosis, Pulmonary embolism |
| Hereditary Orotic Aciduria | Uridine-5'-monophosphate synthase | Block in UMP biosynthesis | Congenital heart disease |
| Hemochromatosis | Unknown autosomal recessive mutation | Excessive absorption of iron leads to iron accumulation in tissues | Congestive cardiomyopathy, arrhythmias |
| Amyloidosis | Prealbumin | Extracellular accumulation of plasma prealbumin (transthyretin) as amyloid | Cardiomyopathy, cardiac conduction defects |
| Zellweger syndrome | Unknown autosomal recessive mutation | Peroxisomes absent or reduced in number leads to defective oxidation and abnormal accumulation of very long chain fatty acids | Patent-ductus arteriosus, septal defects |
| Refsum's disease | Phytanic acid α hydroxylase | Accumulation of phytanic acid in blood and tissues | Nonspecific ECG abnormalities |

Protein mutations can also cause inappropriate function or structure. In these cases, gene therapies, such as RNA interference (RNAi) therapies, are now being developed which would specifically inhibit the production of these mutated proteins and their associated inappropriate function. While this RNAi therapy would prevent the creation of the protein causing the inappropriate function or structural development, it could also lead to a deficiency in the protein and its normal function. This type of interference RNA therapy can thereby also result in a protein deficiency in cardiac cells.

The general classification of known hereditary cardiomyopathy diseases caused by protein mutation include, but are not limited to, dilated cardiomyopathy, hypertrophic cardiomyopathy, and arrhythmogenic right ventricular dysplasia. Another general classification, hereditary arrhythmogenic channelopathies, include, but are not limited to, long QT Syndrome or Brugada Syndrome. These classifications of cardiac diseases are based on a common distinguishing feature of the diseased clinical presentation. While these classifications of cardiac diseases are what is typically used in clinical practice today, each of these disease groups are now known to be caused by one of a number of different mutations and therefore, the clinical disease can be more specifically classified by the underlying protein mutation.

For example, hypertrophic cardiomyopathies are now known to be caused by more than 200 different mutations in ten different proteins. The three most common of these proteins related to hypertrophic cardiomyopathies are shown in the first column of Table 2 located below. In one embodiment, the listed protein in the first column of Table 2 represents at least a portion of the protein that will be delivered as formulation 14. In other embodiments, formulation 14 may contain at least a portion of a protein or proteins that are found in cardiac cells.

TABLE 2

Phenotype Correlations in Hypertrophic Cardiomyopathy

| Mutated Protein | Phenotypic characteristics |
|---|---|
| B-Myosin heavy chain | Early-onset disease; more extensive hypertrophy<br>Higher incidence of sudden death<br>Phenotypic heterogeneity |
| Myosin binding protein C | Mild hypertrophy (60% have LVH by standard criteria)<br>Later onset of LVH and clinical manifestations<br>Lower incidence of sudden death<br>Malignant mutations have been identified |
| Cardiac troponin T | Mild LVH<br>Higher incidence of sudden death |

As another example, Long QT Syndrome is caused by one of a number of different gene mutations of ion channel proteins. The clinical presentation will differ based on the patient's specific mutation. While all Long QT Syndrome patients share the electrophysiologic condition of a lengthened QT interval on their electrocardiogram (ECG), this general clinical condition has a number of distinct phenotypes that are more specifically classified by the gene that is mutated and the aspect of the mutation (characterized by a specific allele). Accordingly, specific risk stratification algorithms and specific proteins are being identified for inherited diseases that can be applied based upon genetic testing of the patient.

Cardiac arrhythmogenic channelopathy diseases are caused by various mutations in a wide number of proteins. The six most common of these proteins related to cardiac arrhythmogenic channelopathies are presented in the third column of Table 3 located below. In one embodiment, the listed protein in the third column of Table 3 represents at least a portion of the protein that will be delivered as formulation 14. In other embodiments, formulation 14 may contain at least a portion of a protein or proteins that are found in cardiac cells.

TABLE 3

Classification of Inherited Arrhythmogenic Channelopathy Diseases

| Disease Channel | Disease Subtype | Defective Protein |
| --- | --- | --- |
| $I_{Ks}$ | LQT1 | KVLQT1 |
| $I_{Ks}$ | LQT5 | MinK |
| $I_{Kr}$ | LQT2 | HERG |
| $I_{Kr}$ | LQT6 | MiRP1 |
| $I_{Na}$ | LQT3, Br-S 1, Lenegre | Nav 1.5 |
| $I_{K1}$ | And-S 1 | Kir2.1 |

Other common cardiac diseases have also been discovered to be caused by any one of a number of proteins. Dilated cardiomyopathies are now known to be caused by mutations in a number of different proteins including: dystrophin, tafazzin, actin, desmin, δ-sarcoglycan, troponin T, β-myosin heavy chain, metavinculin, α-tropomyosin, titin, β-sarcoglyan, and mitochondrial respiratory chain proteins. Furthermore, arrhythmogenic right ventricular dysplasia cardiomyopathy is known to be caused by mutations in a number of different proteins including: ryanodine receptor, desmoplakin, and plakoglobin.

Whether the cause of the protein deficiency is from an inherited genetic mutation, by an environmental agent, or by other therapy, the resulting condition can be severely debilitating or even lead to premature death. Knowing the patient's specific genetic mutation, or the protein being inhibited in the case of RNAi therapy, permits a projection of the disease course and also permits an opportunity for clinical intervention prior to the consequences of the protein deficiency.

Because the mutated proteins associated with many diseases are known, one focus for treating protein deficiencies has been to directly administer the missing protein periodically to the patient through intravenously infusions. Oral administration of therapeutic proteins has not been possible because the complex structure of the protein would be damaged during digestion. Even with intravenous infusion, the therapeutic proteins are quickly filtered by the liver and removed from the blood, and therefore the take-up (endocytocis) by cells in the target organ, such as the heart, may not be sufficient.

In order to deliver an effective dosage, formulation 14 may be co-administered with other molecules in a manner that will optimize cellular uptake of the delivered protein by the cells of the heart. While others have disclosed methods for formulating enzymes for this purpose, specified physical delivery methods or devices for such formulations, such as the implantable source and catheters of the systems and methods described herein, have not been addressed.

In order to ensure the delivery of the sufficient amount of formulation 14, according to embodiments of the present invention, the amount is determined by pericardial sac fluid enzyme level assessment, by blood level assessment, or by projecting the required delivery rate based on the patient's specific genetic mutation and the patient's physical characteristics (e.g., height, weight, genetic sequence of the patient's gene encoding for the protein to be delivered, etc.). This allows the time between source 10 refilling to be maximized while maintaining safe and effective levels of delivery.

Figure 2:
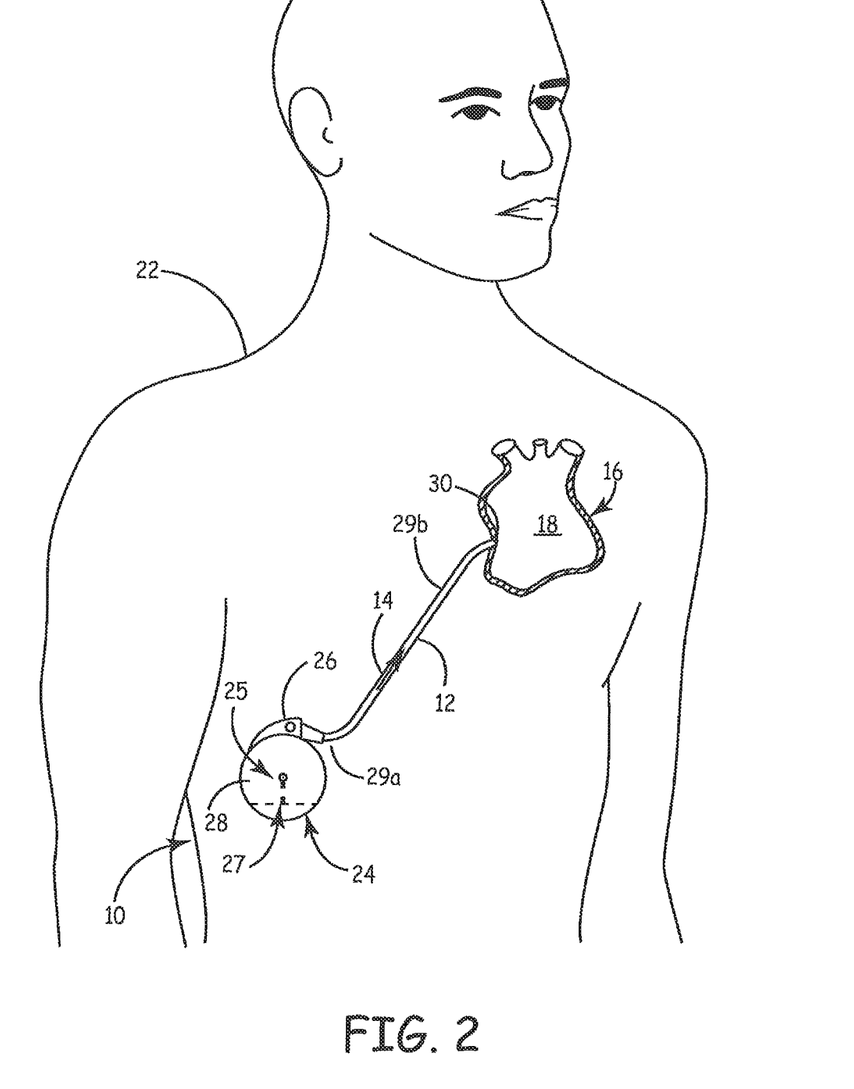
FIG. 2 is a perspective view of a pump and catheter system for delivering proteins to the pericardial sac region.

FIG. 2 is a perspective view of implantable source 10 and catheter 12 for delivering proteins to the pericardial sac region in a human body 22. In this embodiment of the present invention, implantable source 10 is pump 24, which includes inlet port 25, outlet port 26, reservoir 27, and pump mechanism 28.

Inlet port 25 allows reservoir 27 to be filled prior to implantation, and subsequently refilled after pump 24 is surgically implanted into body 22. Reservoir 27 stores formulation 14 prior to delivery to pericardial sac 16. Pump mechanism 28 delivers formulation 14 under pressure to outlet port 26, which is connected to catheter 12.

Proximal end 29a of catheter 12 is coupled to outlet port 26, and distal end 29b with catheter tip 30 is inserted into pericardial sac 16. Catheter tip 30 has a rounded leading exterior surface to minimize tissue disruption during insertion.

Insertion of distal end 29b into pericardial sac 16 allows for the delivery of formulation 14 to cardiac cells due to the relatively slow turn over of the contents within pericardial sac 16.

Distal end 29b can be surgically implanted into pericardial sac 16 of heart 18 using well known stereotactic placement techniques and catheter 12 can be subsequently tunneled subcutaneously through body 22 to the location in body 22 where pump 24 will be implanted. As shown in FIG. 2, pump 24 is surgically implanted subcutaneously in the abdominal region of body 22. In other embodiments, pump 24 may be surgically implanted in other areas of body 22 as in, for example, the pectoral region or under the xyphoid process. Pump 24 may be any number of commercially available implantable infusion pumps such as, for example, the Medtronic SynchroMed pump, model 8611H, or any type of peristaltic, piston, diaphragm, or continuous flow pump.

Figure 3:
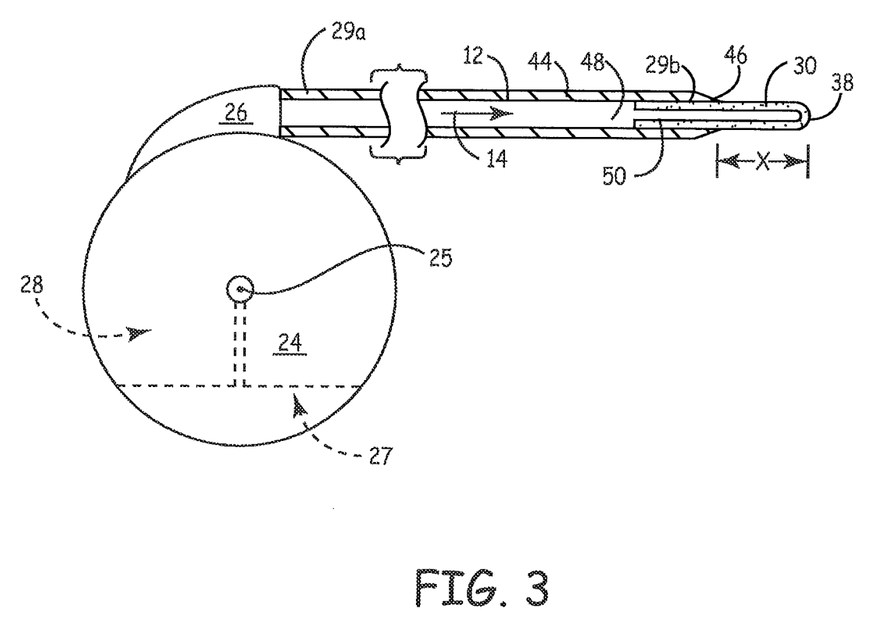
FIG. 3 is a front view of the pump and catheter of FIG. 2.

FIG. 3, shows pump 24 and catheter 12 in further detail. The structures shown in FIG. 3 are exaggerated for ease of illustration of the structure thereof, and the full length of catheter 12 is not shown for simplicity of illustration.

Proximal end 29a of catheter 12 is coupled to outlet port 26. The connection between catheter 12 and outlet port 26 is shown schematically in FIG. 3. The actual type of connection between outlet port 26 and catheter 12 will vary depending upon the particular type of pump 24 utilized.

Inlet port 25, located on the side of pump 24 closest to the front surface of body 22, is used for filling and refilling pump 24 with formulation 14. Once implanted in body 22, pump 24 can be refilled through a syringe and needle that is inserted outside body 22 and into inlet port 25. Formulation 14 is stored in reservoir 27, located inside pump 24.

In one embodiment of the present invention, formulation 14 comprises one or more agents to maintain a physiologically acceptable pH (i.e., a pH or pH range that will not promote degradation of the therapeutic protein) when stored in reservoir 27. In other embodiments, additional or other anti-degradation agents may be added to prevent dissociation of the proteins and/or protein complexes. This is particularly relevant when the programmed delivery rate requires pump 24, with reservoir 27, because the system will be maintained at elevated (i.e., body) temperatures for long periods (i.e., greater than 24 hours), which may potentially promote dissociation of formulation 14.

Catheter 12 comprises an elongated tubular portion 44 that extends from proximal end 29a connected to outlet port 26 and terminates at distal end 29b and tip 30. Catheter tip 30 has a generally rounded leading exterior surface 38 to minimize tissue disruption during insertion. Tubular portion 44 has an externally tapered end surface 46 to again minimize tissue disruption during insertion. Catheter tip 30 has a generally tubular shape and is designed to fit snugly within lumen 48 of tubular portion 44. Catheter tip 30 has a lumen 50 to receive formulation 14 from catheter lumen 48.

Catheter lumen 48 and the external diameter of catheter tip 30 are typically sized so that there is a zero tolerance fit between them. A snug fit is desirable to both maintain the position of catheter tip 30 in relation to tubular portion 44 and to discourage seepage of formulation 14 between the interface of the exterior of catheter tip 30 and the interior surface of tubular portion 44. Under certain conditions, however, catheter 12 may be customized by moving catheter tip 30 in relation to tubular portion 44.

In one embodiment of the present invention, catheter 12 is formed of a material such as silicone, polyethylene, polyamides, polypropylene, or expanded polytetrafluoroethylene. Catheter tip 30 is typically porous along its entire length to enable protein formulation 14 to flow into pericardial sac 16. The typical pore size of catheter tip 30 is approximately less than or equal to about 0.22 microns, to prevent any derelict bacterial agents, that may be present inside catheter 12, from entering pericardial sac 16. Furthermore, at larger pore sizes, there is the potential for tissue in-growth that may restrict the flow of formulation 14 out of catheter tip 30. By making the entire length of catheter tip 30 porous, a more uniform volume distribution of formulation 14 is provided. Pore size can be adjusted to allow for the delivery of a specific protein while still preventing in-growth and preventing bacterial agents from entering into pericardial sac 16.

Catheter tip 30 can use a single or multiple elution hole format. Alternatively, catheter tip 30 dispenses formulation 14 in a nearly 360 degree pattern along the entire length of catheter tip 30 that is exposed to pericardial sac 16, represented in FIG. 3 by the length "X". Length X may be custom selected by a physician at the time of insertion. To enable the physician to customize length X, tubular portion 44 is typically comprised of a material that will expand in response to an external stimulus such as heat or a chemical solvent.

When tubular portion 44 expands in response to the external stimulus, the snug fit between catheter tip 30 and tubular portion 44 is relieved and the physician may slide catheter tip 30 with respect to tubular portion 44 by hand to achieve the desired length X. When the external stimulus is removed, tubular portion 44 returns to its ordinary shape, thereby reestablishing the near zero tolerance fit between tubular portion 44 and catheter tip 30.

Pump 24 can be programmed to deliver a specific amount of therapeutic protein formulation at a precise rate or programmed rate ramp. This can be done non-invasively with a Medtronic Model 8821 Programmer, or other suitable programmers. Programmable rates provide for a controlled dosing regimen, allowing for the avoidance of toxic side-affects of treatment and sudden down stream build up of substrate. The programmable delivery rate is selected based on factors including the specific cardiac disorder, genetic sequence of the patient=s gene encoding for the protein to be delivered, body weight, and various combinations thereof.

Figure 4:
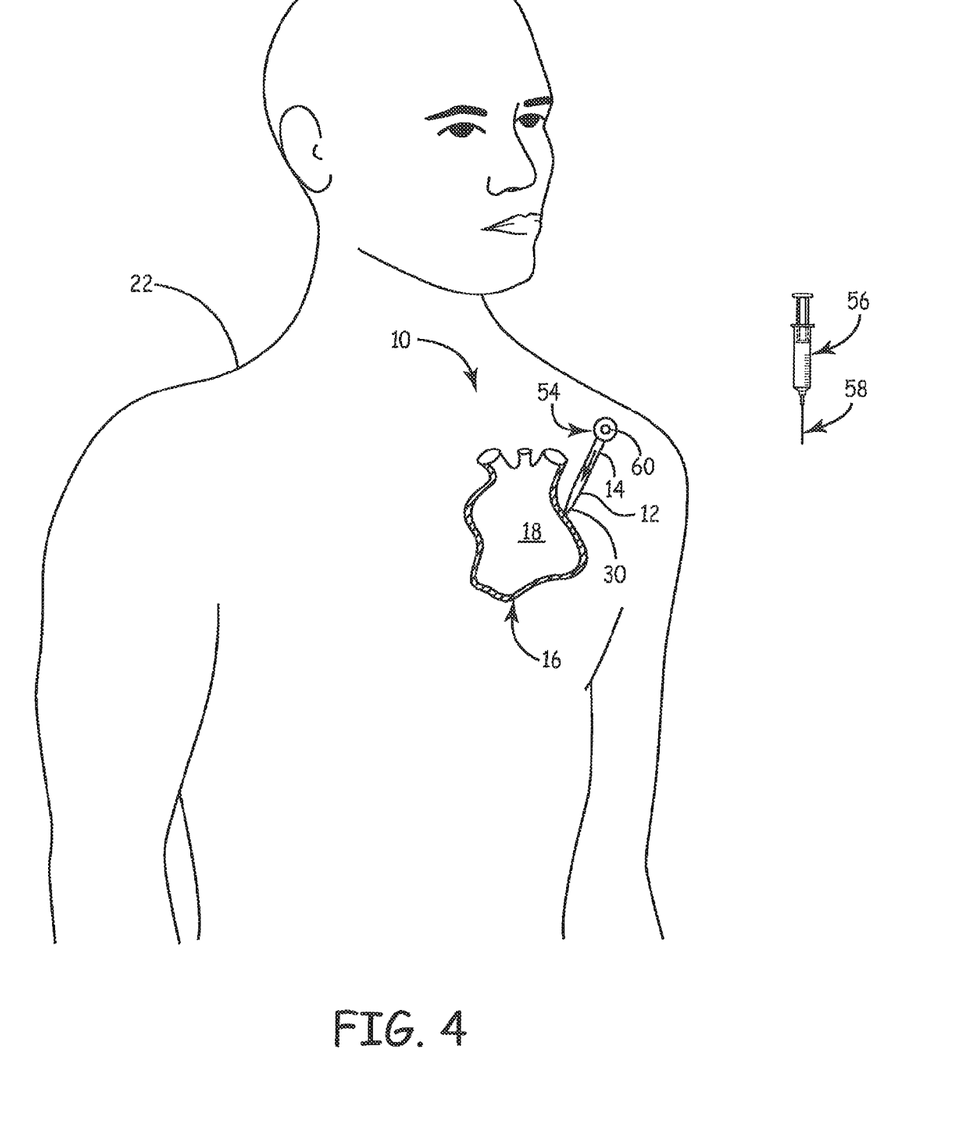
FIG. 4 is a perspective view of an access port and catheter system for delivering proteins to the pericardial sac region.

FIG. 4 is a perspective view of source 10 delivering protein formulation 14 through catheter 12 to pericardial sac 16. In this embodiment, source 10 is access port 54, which is a receptacle to receive and deliver a bolus of formulation 14 through catheter 12 to pericardial sac 16. Access port 54 can be of a wide variety of suitable inlet or injection ports that are commonly used in the medical device field, and allows for a continuous steady flow of a single dosage of formulation 14 to pericardial sac 16. Once access port 54 is surgically implanted into body 22, a dosage of formulation 14 is delivered by syringe 56. Needle 58 of syringe 56 is placed through the patient=s skin into inlet 60 located on the side of access port 54 closest to the front surface of body 22. The pressure exerted by the plunger of syringe 56 delivers formulation 14 through needle 58, access port 54, and catheter 12 into pericardial sac 16.

FIG. 4 shows access port 54 implanted above heart 18, under the left pectoral muscle. Catheter 12 extends out of access port 54 and runs parallel to heart 18 for a short distance and then penetrates into pericardial sac 16 with tip 30. In other embodiments access port 54 can be placed in other regions of body 22 as in, for example, the abdomen or under the right pectoral muscle.

It will be understood that specific structures, functions, and operations set forth can be practiced in conjunction with the present invention, but they are not essential to its practice. It is therefore to be understood that the invention may be practiced otherwise than as specifically described without actually departing from the spirit and scope of the present invention as defined by the appended claims.

What is claimed is:

1. A method comprising:
   delivering a therapeutic protein formulation from an implantable source through an implantable catheter directly to a pericardial sac region of a heart of a patient,
   wherein the patient has a cardiac disorder caused by a protein deficiency due to a gene mutation,
   wherein the therapeutic protein formulation comprises a protein in a form that is deficient in cardiac cells of the patient due to the gene mutation,
   wherein the therapeutic protein formulation is delivered at a rate based on the sequence of the patient's gene encoding the deficient protein; and
   wherein the cardiac disorder and the protein deficiency are selected from:
   Mucopolysaccharidoese Hurler (MPS IH) and α-L-iduronidase;
   Schie (MPS IS) and α-L-iduronidase;
   Hunter (MPS II) and Sulfoiduranate sulfate;
   Marquio syndrome (Mucopolysaccharidosis II) and β-Galactosidase;
   Maroteaux-Lamy syndrome (MPS VI) and Aryl sulfatase B;
   Mucolipidoses I cell disease (Mucolipidosis II) and N-acetylglucosamine-I-phosphotransferase;
   PseudoHurler polydystrophy (Mucolipidoses III) and N-acetylglucosamine-I-phosphotransferase;
   Sphingolipidoses Gaucher disease Type I and Glucocerebrosidase;
   Type III Glycogenosis and Amlo-1,6-glucosidase;
   Acyl-CoA Dehydrogenase Deficiencies LCAD Deficiency and Long-chain acylCoA dehydrogenase;
   Primary Hyperoxaluria I and Alumine: glyoxylate amino transferase;
   Primary Hyperoxaluria II and D-glyceric acid dehydrogenase;
   Homocystinuria and Cystathionine;
   Triose-phosphate isomerase deficiency and Triose-phosphate isomerase;
   Hereditary Orotic Aciduria and Uridine-5'-monophosphate synthase;
   Amyloidosis and Prealbumin; and
   Refsum's disease and Phytanic acid α hydroxylase.

2. The method of claim 1, wherein the protein formulation comprises at least one stabilizing agent or anti-degradation agent operable for maintaining a desired pH.

3. The method of claim 1, wherein the implantable source comprises a refillable reservoir to store the protein formulation.

4. The method of claim 1, further comprising administering an RNA interference therapy to the patient to inhibit production of a mutated protein resulting from the gene mutation.

5. The method of claim 1, wherein the rate of delivery of the therapeutic protein formulation is further based on assessment of cardiac tissue enzyme level in the patient.

6. A method comprising:
   determining a rate of delivery of a therapeutic protein formulation from an implantable source through an implantable catheter directly to a pericardial sac region of a heart of a patient,
      wherein the patient has a cardiac disorder caused by a protein deficiency due to a gene mutation,
      wherein the therapeutic protein formulation comprises a protein in a form that is deficient in cardiac cells of the patient due to the gene mutation, and
      wherein the therapeutic protein formulation is delivered at a rate based on the the sequence of the patent's gene encoding the deficient protein;
   delivering the therapeutic protein formulation from the implantable source through the implantable catheter directly to the pericardial sac region of the heart of the patient; and
   wherein the cardiac disorder and the protein deficiency are selected from:
      Mucopolysaccharidoese Hurler (MPS IH) and α-L-iduronidase;
      Schie (MPS IS) and α-L-iduronidase;
      Hunter (MPS II) and Sulfoiduranate sulfate;
      Marquio syndrome (Mucopolysaccharidosis II) and β-Galactosidase;
      Maroteaux-Lamy syndrome (MPS VI) and Aryl sulfatase B;
      Mucolipidoses I cell disease (Mucolipidosis II) and N-acetylglucosamine-I-phosphotransferase;
      PseudoHurler polydystrophy (Mucolipidoses III) and N-acetylglucosamine-I-phosphotransferase;
      Sphingolipidoses Gaucher disease Type I and Glucocerebrosidase;
      Type III Glycogenosis and Amlo-1,6-glucosidase;
      Acyl-CoA Dehydrogenase Deficiencies LCAD Deficiency and Long-chain acylCoA dehydrogenase;
      Primar Hyperoxaluria I and glyoxylate amino transferase;
      Primary Hyperoxaluria II and D-glyceric acid dehydrogenase;
      Homocystinuria and Cystathionine;
      Triose-phosphate isomerase deficiency and Triose-phosphate isomerase;
      Hereditary Orotic Aciduria and Uridine-5'-monophosphate synthase;
      Amyloidosis and Prealbumin; and
      Refsum's disease and Phytanic acid α hydroxylase.

7. The method of claim 6, wherein determining the rate of delivery of the therapeutic protein formulation is further based on assessment of cardiac tissue enzyme level in the patient.

8. A method comprising:
   injecting a therapeutic protein formulation into an implantable source; and
   delivering the therapeutic protein formulation from an implantable source through an implantable catheter directly to a pericardial sac region of a heart of a patient,
      wherein the patient has a cardiac disorder caused by a protein deficiency due to a gene mutation,
      wherein the therapeutic protein formulation comprises a protein in a form that is deficient in cardiac cells of the patient due to the gene mutation, and
      wherein the therapeutic protein formulation is delivered at a rate based on the sequence of the patient's gene encoding the deficient protein;
   wherein the cardiac disorder and the protein deficiency are selected from:
      Mucopolvsaccharidoese Hurler (MPS IH) and α-L-iduronidase;
      Schie (MPS IS) and α-L-iduronidase;
      Hunter (MPS II) and Sulfoiduranate sulfate;
      Marquio syndrome (Mucopolysaccharidosis II) and β-Galactosidase;
      Maroteaux-Lamy syndrome (MPS VI) and Aryl sulfatase B;
      Mucolipidoses I cell disease (Mucolipidosis II) and N-acetylglucosamine-I-phosphotransferase;
      PseudoHurler polydystrophy (Mucolipidoses III) and N-acetylglucosamine-I-phosphotransferase;
      Sphingolipidoses Gaucher disease Type I and Glucocerebrosidase;
      Type III Glycogenosis and Amlo-1,6-glucosidase;
      Acyl-CoA Dehydrogenase Deficiencies LCAD Deficiency and Long-chain acylCoA dehydrogenase;
      Primary Hyperoxaluria I and Alumine: glyoxylate amino transferase;
      Primary Hyperoxaluria II and D-glyceric acid dehydrogenase;
      Homocystinuria and Cystathionine;
      Triose-phosphate isomerase deficiency and Triose-phosphate isomerase;
      Hereditary Orotic Aciduria and Uridine-5'-monophosphate synthase;
      Amyloidosis and Prealbumin; and
      Refsum's disease and Phytanic acid α hydroxylase.

9. The method of claim 8, wherein the rate of delivery of the therapeutic protein formulation is further based on assessment of cardiac tissue enzyme level in the patient.

* * * * *